(12) United States Patent
Zhang et al.

(10) Patent No.: US 7,767,465 B2
(45) Date of Patent: Aug. 3, 2010

(54) REDUCTION OF PLATELET INTERFERENCE IN PLASMA ASSAY SAMPLES

(75) Inventors: Bin Zhang, Old Brookville, NY (US); E. Sabrinah Chapman-Montgomery, Croton on Hudson, NY (US); Edward P. Kang, Garden City, NY (US)

(73) Assignee: Siemens Healthcare Diagnostics Inc, Tarrytown, NY (US)

( * ) Notice: Subject to any disclaimer, the term of this patent is extended or adjusted under 35 U.S.C. 154(b) by 382 days.

(21) Appl. No.: 11/685,289

(22) Filed: Mar. 13, 2007

(65) Prior Publication Data

US 2007/0224651 A1 Sep. 27, 2007

Related U.S. Application Data

(60) Provisional application No. 60/781,865, filed on Mar. 13, 2006.

(51) Int. Cl.
*G01N 1/00* (2006.01)
(52) U.S. Cl. .................... 436/175; 435/2; 435/7.1; 436/17; 436/18; 436/174; 436/176; 436/177
(58) Field of Classification Search ............ 435/2, 435/7.1; 436/17, 18, 174, 175, 176, 177
See application file for complete search history.

(56) References Cited

U.S. PATENT DOCUMENTS

| | | | | |
|---|---|---|---|---|
| 4,389,490 A | 6/1983 | Crews et al. | ............. | 436/17 |
| 5,196,182 A | 3/1993 | Ryan | ............. | 424/3 |
| 5,250,438 A | 10/1993 | Ryan | ............. | 436/17 |
| 5,260,048 A | 11/1993 | Ryan | ............. | 424/3 |
| 5,459,073 A | 10/1995 | Ryan | ............. | 436/16 |
| 5,460,797 A | 10/1995 | Ryan | ............. | 435/40.5 |
| 5,811,099 A | 9/1998 | Ryan | ............. | 424/184.1 |
| 5,849,517 A | 12/1998 | Ryan | ............. | 435/40.5 |
| 6,337,189 B1 | 1/2002 | Ryan | ............. | 435/40.5 |
| 6,449,562 B1 * | 9/2002 | Chandler et al. | ............. | 702/19 |
| 6,475,801 B1 | 11/2002 | Nishizaki et al. | ............. | 436/69 |
| 6,939,678 B1 * | 9/2005 | Buechler et al. | ............. | 435/7.1 |
| 6,977,156 B2 * | 12/2005 | Ryan et al. | ............. | 435/7.2 |
| 2004/0137417 A1 | 7/2004 | Ryan | | |
| 2008/0206866 A1 * | 8/2008 | Zieglschmid et al. | ............. | 435/375 |

FOREIGN PATENT DOCUMENTS

| | | |
|---|---|---|
| WO | 92/19951 A1 | 11/1992 |
| WO | WO 9906829 | 2/1999 |
| WO | WO 2005036123 A2 | 4/2005 |
| WO | PCT/US2007/006289 | 3/2007 |

OTHER PUBLICATIONS

PCT International Search Report dated May 21, 2008 for corresponding PCT/US07/06289.
U.S. Appl. No. 60/775,161, filed Feb. 21, 2006, Jou Josep Maria.

* cited by examiner

*Primary Examiner*—Gailene R Gabel
(74) *Attorney, Agent, or Firm*—Woodcock Washburn; Noam R. Pollack

(57) ABSTRACT

The present invention relates to compositions for improving assay accuracy for plasma samples by decreasing or eliminating false results due to platelet interference. The compositions of the present invention comprise compositions that include a platelet interference reducing agent in an amount effective to decrease the platelet interference activity in the plasma sample, particularly platelet-rich plasma sample, to be analyzed. The most preferred platelet interference reducing agent of the present invention is 1-(1,3-Bis(hydroxymethyl-2,5-dioxoimidazolidin-4-iyl)-1,3-bis(hydroxymethyl) urea, also called "Diazolidinyl urea" or "DZU".

9 Claims, 1 Drawing Sheet

REDUCTION OF PLATELET INTERFERENCE IN PLASMA ASSAY SAMPLES

CROSS REFERENCE TO RELATED APPLICATIONS

This application claims benefit of U.S. Provisional Application No. 60/781,865, filed Mar. 13, 2006, the disclosure of which is hereby incorporated by reference in its entirety.

FIELD OF THE INVENTION

This invention relates to the field of analytical methods for determining, quantitatively and/or qualitatively, the presence of an analyte in a biological fluid, and, in particular, a biological fluid such as plasma. Although the present invention will be described below in context of its use in automated analytical assays and methods, the present invention may also be used with manual and semi-automated assays and methods.

BACKGROUND

The medical industry has become increasingly dependent upon the ability to measure various entities in physiological fluids in order to be able to determine the health status of an individual, dosage level for drugs, use of illegal drugs, genomic sequences, and the like. Thus, the capability of taking a physiological sample and rapidly analyzing for a particular component has made medical therapies more efficient and increasingly successful.

In many instances, one wishes to use plasma as a source to diagnose a patient's health or to monitor the efficacy of drugs that have been administered to the patient. Plasma as a source for the determination of these parameters may have some difficulties. For example, it is well-known in the art that plasma samples containing platelets are still hampered by problems of inaccuracy, lack of precision, and lack of reproducibility. These properties complicate the use of plasma as a sample for diagnostic purposes.

There is, therefore, substantial interest in devising new approaches for using and manipulating plasma for diagnostic purposes. One area of particular interest is the reduction or elimination of platelet interference. When a plasma sample has been properly centrifuged and properly handled after the centrifuging step, a visible upper layer, called the "buffy layer" forms in the sample tube. The buffy layer should contain much of, if not the majority of, the platelets in the sample to minimize platelet interference. Depending upon the centrifugation process, namely length of time of centrifugation and gravitational force, upon completion of centrifugation, the sample will either be a "platelet rich" plasma sample or a "platelet poor" plasma sample. As the terms imply, a "platelet rich" plasma sample contains a significant quantity of platelets in the non-buffy layer portion of the sample as compared to a "platelet poor" plasma sample.

Quantitatively, if the hematocrit (the measure of the volume of red blood cells as a percentage of the total blood volume) of a whole blood sample is approximately 30%, such whole blood sample (i.e., a sample that has not been subjected to centrifugation) can contain as much as about 63% of the number of platelets found in a platelet rich plasma sample. Thus, given a hematocrit of about 30%, platelet rich plasma will comprise about $6.55 \times 10^5$ platelets per microliter of sample, and the whole blood platelet count will be about $4.12 \times 10^5$ platelets per microliter (about 63% of the number of platelets per microliter in the platelet rich plasma sample). The reference range of platelets in whole blood is about $1.5 \times 10^5$ to about $4.5 \times 10^5$ platelets per microliter, which means that a platelet rich plasma sample can have a platelet count of more than $2.0 \times 10^6$ platelets per microliter. A platelet poor plasma sample can have a platelet count of less than $1.0 \times 10^4$ platelets per microliter.

Proper transfer and insertion of the sample tube into the appropriate analytical device after centrifuging minimizes platelet interference in the measurement of the relevant analyte. However, mishandling of sample tubes can occur frequently. For example, the sample may not be centrifuged properly, either being centrifuged for too short a time period or at too low a gravitational force. Alternatively, even if the sample is properly centrifuged, mishandling of the sample tube, e.g., by subsequent agitation or inversion by the human handler, can result in platelets redispersing through the sample, thereby interfering with the measurement of the analyte, and providing a false result. Furthermore, when a false result is suspected, additional tests may be required. This results in wasted resources, both in terms of time and money. Worse yet, a false result may result in severe complications to the patient if the false result is the basis for treatment.

Moreover, for certain STAT assays (i.e., assays that are preferably performed within a short period of time following sample acquisition) such as for hCG and cardiac markers (e.g., CKMB, Troponin I), centrifuging time for the preparation of plasma is sometimes further reduced by clinical laboratories in order to minimize the time that elapses before results can be obtained. With the reduced centrifugation time, the resulting plasma samples will have higher platelet concentrations, which magnifies the platelet interference problem.

Also, as efficiency becomes critical in laboratory environments to reduced cost, increased revenue, and decreased time for providing clinicians with laboratory results, it is greatly desired to have a means by which plasma test samples can be made more "robust". Plasma samples are more "robust" when they are less susceptible to platelet interference (a) without decreasing efficiency (e.g., without significantly increasing centrifuge time) or (b) without increasing false results (i.e., false positives or false negatives). It can be especially useful and economically valuable if an assay can be conducted more quickly (e.g., by decreasing centrifuging time), while maintaining the robustness of the assay and reducing the incidence of false results. Under ideal circumstances, a false results rate of <5% will be observed with respect to a given assay, but such a low proportion of false results is not normally attained.

Previous attempts have been made to achieve these ends: centrifuging samples, high dilution, addition of anticoagulants, and the like. However, as mentioned above, increasing centrifuge time decreases laboratory efficiency and decreases quality of patient care since it increases the time that is required to obtain test results. Another strategy for addressing this issue involved the addition of anticoagulants to plasma samples, but the results of such strategies have not been favorable. Accordingly, there remains a need for methods that are effective in reducing the incidence of platelet interference in plasma samples, while maintaining or increasing the efficiency of the process of preparing such samples for subsequent analysis.

SUMMARY

Provided are methods comprising contacting a sample comprising platelets with a composition comprising diazolidinyl urea, thereby forming a combination; and, measuring at least one analyte in the combination.

Also provided are methods for evaluating the efficacy of a treatment regimen comprising contacting a sample comprising platelets of a subject undergoing said treatment regimen with a composition comprising diazolidinyl urea, thereby forming a combination; measuring one or more analytes in the combination; and, based on the measurement of the one or more analytes, evaluating the efficacy the treatment regimen for the subject.

There are also disclosed methods for prospectively determining an appropriate treatment regimen comprising contacting a sample comprising platelets of a subject with a composition comprising diazolidinyl urea, thereby forming a combination; measuring one or more analytes in the combination; and, based on the measurement of the one or more analytes, selecting a treatment regimen for the subject.

Also provided are methods for preparing a sample comprising platelets comprising obtaining a sample comprising platelets, centrifuging the sample comprising platelets, and contacting the sample comprising platelets with a composition comprising diazolidinyl urea, thereby forming a combination.

DETAILED DESCRIPTION OF ILLUSTRATIVE EMBODIMENTS

Figure 1:
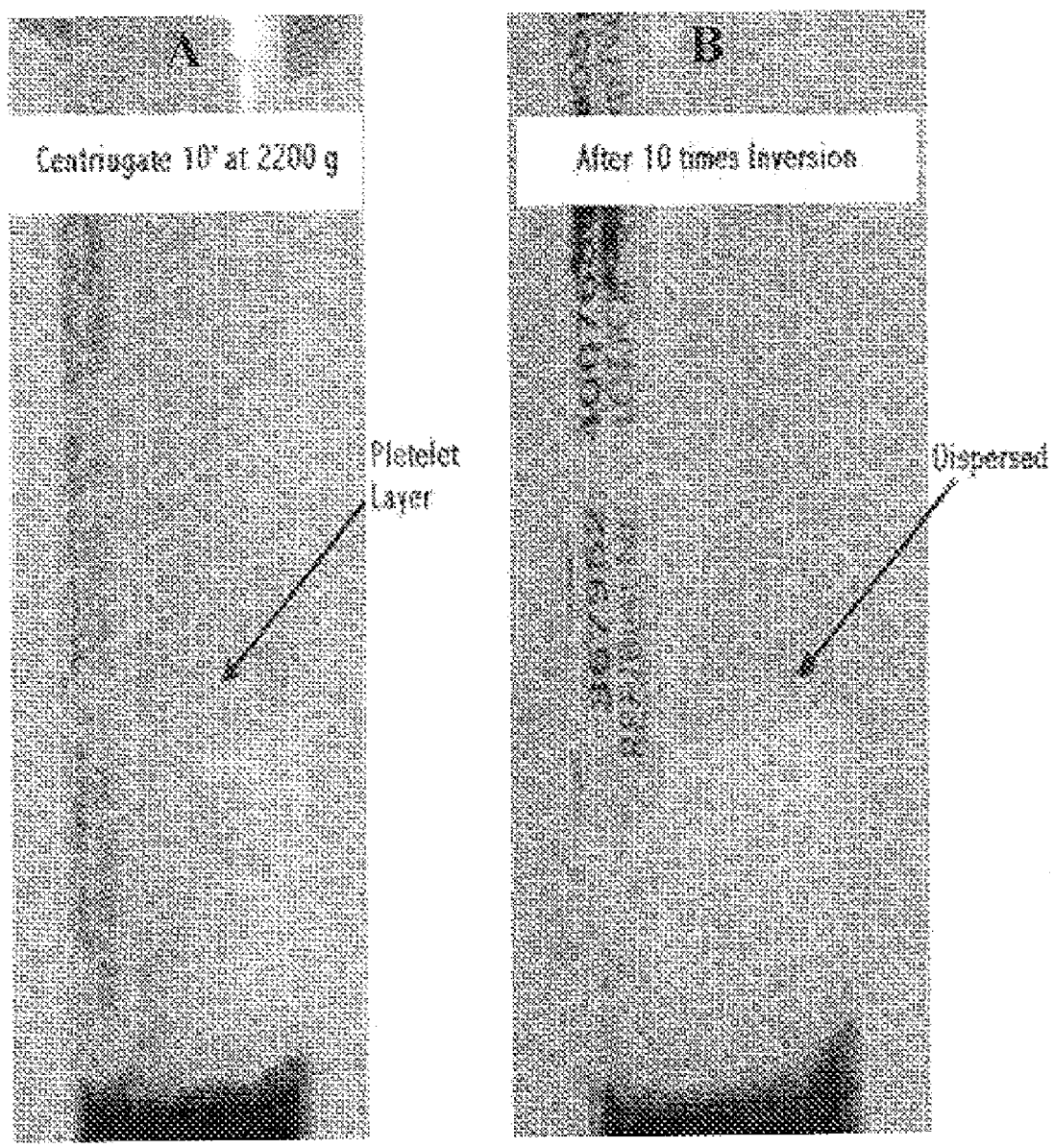
FIG. 1 is a comparison of a blood sample tube before and after ten inversions of the tube.

The present invention may be understood more readily by reference to the following detailed description taken in connection with the accompanying figure and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. Thus, for example, a reference to "an analyte" is a reference to one or more of such analytes and equivalents thereof known to those skilled in the art, and so forth. When values are expressed as approximations, by use of the antecedent "about," it will be understood that the particular value forms another embodiment. As used herein, "about X" (where X is a numerical value) refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable.

The present invention relates to compositions for improving assay accuracy for plasma samples by decreasing or eliminating false results due to platelet interference. The compositions comprise a platelet interference reducing agent in an amount effective to decrease the interference of platelets on the assay, thereby causing false results. The most preferred platelet interference reducing agent of the present invention is 1-(1,3-Bis(hydroxymethyl-2,5-dioxoimidazolidin-4-iyl)-1, 3-bis(hydroxymethyl) urea, also referred to as "Diazolidinyl urea" or "DZU".

While DZU has been used in whole blood samples, e.g., as a preservative (see, for example, U.S. Pat. No. 6,977,156), it was heretofore unknown that the addition of DZU to plasma samples could profoundly inhibit false results from platelets and/or decrease centrifuging time required to displace platelets from the portion of plasma sample to be analyzed. Other references that disclose use of DZU as a fixative or preservative of cells or tissue: U.S. Pat. Nos. 6,337,189; 5,849,517; 5,811,099; 5,460,797; 5,260,048; 5,250,438; 5,196,182; and, 5,459,073.

The present invention also relates to methods for detecting or measuring an analyte in a plasma sample that includes a platelet interference reducing agent in an amount effective to decrease false results. The most preferred platelet interference reducing agent of this aspect of the present invention is DZU.

The present invention further relates to methods for decreasing/eliminating the effect of platelet interference in detecting or measuring an analyte in a plasma sample. Such methods use compositions that include a platelet interference reducing agent in an amount effective to decrease platelets interference. The most preferred platelet interference reducing agent of this aspect of the present invention is DZU.

The invention will partly be described herein with respect to an assay formulated to measure human choriongonadotropin (also referred to as "human chorionic gonadotropin", hereinafter referred to as "hCG"). However, the present invention can be effective for any plasma-based assay. The present invention is especially effective for use in plasma-based assays that can be affected by platelet interference, such as, for example, CKMB and Troponin I, or for any plasma-based assay for which the goal is to reduce centrifuging time and/or minimizing false results. The methods of the invention are especially useful for reducing centrifuge time and/or reducing false results when applied to platelet-rich plasma assays.

Provided are methods comprising contacting a sample comprising platelets with a composition comprising diazolidinyl urea, thereby forming a combination; and, measuring at least one analyte in the combination.

As used herein, the term "combination" or "combining" or derivatives thereof refers to a collection of substances that have been combined via any physical and/or chemical process, or to the act of forming a collection of substances via any physical and/or chemical process. A "sample comprising platelets" is a material that includes platelets or components thereof. Nonlimiting examples of samples comprising platelets include human or animal blood or plasma.

With respect to any of the present methods, the contacting of the sample comprising platelets with the composition comprising diazolidinyl urea is preferably effected by adding the respective substances to a vessel, such as a sample collection tube. The sample collection tube can be a blood collection tube, many types of which are commercially available. For example, the sample collection tube can be a Becton Dickinson Vacutainer® blood collection tube (Becton, Dickinson and Company, Franklin Lakes, N.J.). The sample collection tube can contain heparin, including, for example, a Becton Dickinson Vacutainer® Heparin Tube (Becton, Dickinson and Company, Franklin Lakes, N.J.). In exemplary embodiments, the sample comprising platelets is collected into a sample collection vessel, and the composition comprising diazolidinyl urea is subsequently added. In other instances, the composition comprising diazolidinyl urea is added to a sample collection vessel, into which the sample comprising platelets is subsequently introduced. The instant invention encompasses the combination of a sample comprising platelets and composition comprising diazolidinyl urea in any order, sequence, or progression.

DZU can be used in any embodiment of the present invention at levels as low as about 1.5 wt % (15 g/L) to as high as about 7.0 wt % (70 g/L). In preferred embodiments, DZU is used in the present invention at from about 3.0 wt % (30 g/L) to about 7.0 wt % (70 g/L), more preferably from about 3.0 wt % (30 g/L) to about 6.0 wt % (60 g/L), and most preferably about 4.5 wt % (45 g/L) to about 5.5 wt % (55 g/L). The foregoing weight percents (wt %) are based upon the total weight of the combination.

It is preferred that the sample comprising platelets is kept at a neutral to slightly acidic pH. The present invention may be practiced when the pH is from about 4.8 to about 7.1. However, preferably, the pH is about 6.0 to about 7.0, and more preferably, the pH is about 6.4 to about 6.8.

The elapsed time between the collection of the sample comprising platelets and the contacting of the sample comprising platelets with the composition comprising diazolidinyl urea therewith is ideally brief, and preferably occurs over a matter of minutes, and even more preferably over a matter of seconds. Thus, for example, a sample comprising platelets may comprise blood that is collected from a subject at a starting time, and the combining of the blood with the composition comprising diazolidinyl urea can occur within about five minutes following such starting time. Preferably, the combining of the sample comprising platelets with the other member(s) of the combination occurs within about three minutes or less following the acquisition of the sample comprising platelets, although longer periods of time are also contemplated as being within the scope of the instant invention. Gentle mixing of the resulting combination, for example, by carefully inverting the sample collection tube one or more times (inverting the tube seven to eight times being a preferred embodiment), preferably follows the combining step. The combination may subsequently be subjected to analysis using the ADVIA® 120 or 2120 Hematology System (Bayer AG, Leverkusen, Germany). Processing of the combination through the ADVIA® system can take an additional period of time, preferably not more than about five minutes.

Following the contacting step, the combination can be stored, for example, pending subsequent use. Alternatively or additionally, the combination can be centrifuged so that, for example, the "buffy layer" is formed. Centrifugation processes are widely practiced in the art and the skilled practitioner will be able to identify appropriate centrifugation regimes, both in terms of duration and applied gravitational force.

In other embodiments, the sample comprising platelets is subjected to centrifugation prior to the contacting of the sample with the composition comprising diazolidinyl urea.

With or without a centrifugation step, the contacting step can be followed by measuring at least one analyte in the combination. The measuring can be performed using one or more immunoassays, although other methods of detecting the at least one analyte are also contemplated. The immunoassay can comprise a STAT assay, such as a human choriongonadotropin (hCG) assay and/or a cardiac marker assay.

In some embodiments of the disclosed methods, the incidence of false results in the combination is about 10% less than the incidence of false results observed with respect to samples comprising platelets that have not been contacted with a composition comprising diazolidinyl urea (hereafter referred to as "untreated samples comprising platelets"). "False results" can refer to false positives or false negatives, or both. A comparison between the combination (i.e., the sample comprising platelets that has been contacted with a composition comprising diazolidinyl urea) and the untreated samples comprising platelets may be made in instances where neither have been inverted, or where both have been inverted one or more times. In instances where both the combination and the untreated samples comprising platelets have been inverted one or more times, the incidence of false results in the combination can be about 10% less, about 30% less, about 50% less, or about 70% less than the incidence of false results observed with respect to the untreated samples comprising platelets. In other embodiments, false results in the combination occur with a frequency of about 10% or less, and in still other embodiments, false results occur with a frequency of about 5% or less.

Also provided are methods for evaluating the efficacy of a treatment regimen comprising contacting a sample comprising platelets of a subject undergoing said treatment regimen with a composition comprising diazolidinyl urea, thereby forming a combination; measuring one or more analytes in the combination; and, based on the measurement of the one or more analytes, evaluating the efficacy the treatment regimen for the subject.

The methods for evaluating the efficacy of a treatment regimen may further comprise measuring at least a subset of the one or more analytes in a sample comprising platelets of the subject prior to the initiation of the treatment regimen. Thus, the disclosed methods can result in the measurement of several analytes, for example, analytes $A^1$, $A^2$, and $A^3$, in a sample comprising platelets of a subject before that subject has undergone the treatment regimen. The instant methods can further comprise comparing the measurement of the one or more analytes with the measurement of the at least a subset of the analytes. For example, therefore, the present methods can include comparing the measurement of analytes $A^1$, $A^2$, $A^3$, and $A^4$ (such measurement having been made in a sample comprising platelets of a subject that was already undergoing the treatment regimen) with the measurement of at least a subset, for example, of analytes $A^1$, $A^2$, and $A^3$, such measurement having been made in a sample comprising platelets of the subject before the subject has undergone the treatment regimen.

The present methods can also comprise measuring at least a subset of the one or more analytes in a sample comprising platelets of the subject at some timepoint during the treatment regimen that precedes the measuring of the one or more analytes. Thus, the disclosed methods can result in the measurement of several analytes, for example, analytes $A^1$, $A^2$, and $A^3$, in a sample comprising platelets of a subject at some point in time during the treatment regimen that precedes the measuring of analytes $A^1$, $A^2$, $A^3$, and optionally additional analytes in accordance with the claimed methods. Furthermore, the instant methods can also comprise comparing the measurement of the one or more analytes with the measurement of the at least a subset of the analytes. For example, therefore, the present methods can include comparing the measurement of analytes $A^1$, $A^2$, $A^3$, and $A^4$ (such measurement having been made in a sample comprising platelets of a subject at a timepoint t=1) with the measurement of the at least a subset, for example, of analytes $A^1$, $A^2$, $A^3$, and $A^4$, such measurement having been made in a sample comprising platelets of the subject at some earlier timepoint than t=1 during the treatment regimen.

There are also disclosed methods for prospectively determining an appropriate treatment regimen comprising contacting a sample comprising platelets of a subject with a composition comprising diazolidinyl urea, thereby forming a combination; measuring one or more analytes in the combination; and, based on the measurement of the one or more analytes, selecting a treatment regimen for the subject.

As for any embodiment of the present invention, the measuring can be performed using one or more immunoassays, although other methods of detecting the at least one analyte are also contemplated. The immunoassay can comprise a STAT assay, such as a human choriongonadotropin (hCG) assay and/or a cardiac marker assay.

Also provided are methods for preparing a sample comprising platelets, e.g., so that the sample comprising platelets is in an advantageous condition for analysis, comprising obtaining a sample comprising platelets, centrifuging the sample comprising platelets, and contacting the sample comprising platelets with a composition comprising diazolidinyl urea, thereby forming a combination.

One benefit that is provided by the present methods for preparing a sample comprising platelets comprises a decrease in the incidence of platelet interference, even with reduced centrifuge time as compared with the centrifugation time required for adequate preparation of samples comprising platelets that have not been prepared in accordance with the present methods. Presently, the processing of samples comprising platelets that have not been prepared in accordance with the instant methods can involve centrifugation at 2,200 g for 20 minutes (which results in a platelet rich plasma sample). In some embodiments of the present invention, the centrifugation time can be about 30% less than the time required for samples comprising platelets that have not been prepared in accordance with the instant methods. In other embodiments, the centrifugation time can be about 50% less than the time required for samples comprising platelets that have not been prepared in accordance with the instant methods. The centrifugation time for samples to be prepared in accordance with instant methods can be about 14 minutes at 2,200 g; the centrifugation time can also be about 10 minutes at 2,200 g.

While the inventors do not wish to be bound by any one theory, it is believed that the addition of platelet interference reducing agent decreases the thrombotic activity of the platelets. Without wishing to be bound by any one theory, the mechanism of action may be because (a) the platelet interference reducing agent physically segregates the platelets from the sample portion to be analyzed, (b) the platelet interference reducing agent chemically inactivates the thrombotic/clotting activity of the platelets, (c) or some combination thereof.

EXAMPLE 1

First, to determine the source of the false results, experiments were conducted to confirm that platelets do play a role in engendering false positive results. Several plasma samples that had been mixed or otherwise disturbed were measured for hCG using the ADVIA IMS® Integrated Modular System available from Bayer Healthcare LLC, Diagnostics Division, Tarrytown, N.Y. The report showed that platelets do play a role in the false positive results for the hCG assay. For example, when platelets in the plasma samples are mixed or disturbed, hCG results for negative samples can be falsely elevated to be as high as 150 mIU/mL. Upon re-centrifugation of these samples, hCG recoveries decreased significantly and became normal.

FIG. 1 illustrates the comparison of a platelet layer properly separated from plasma (FIG. 1A) and the redistribution and disappearance of the buffy layer after the test tube was inverted ten times (FIG. 1B). The platelet counts in the serum portion, as determined on the ADVIAR® 120 instrument (Bayer Healthcare LLC, Diagnostics Division, Tarrytown, N.Y.), correlated with the false positive results. In other words, as the number of platelets redistributed through the serum increased, the extent of false positive results also increased. Thus, the disturbance or redistribution of platelets through the plasma sample was confirmed to be the "trigger" for the false results received for the hCG assays. While not intending to be bound by any one theory, it is believed that the dispersion/redispersion of platelets into the plasma sample causes false results, particularly false positive results, for hCG assays by significantly increasing non-specific binding of alkaline phosphatase conjugates to the solid phase of the assay.

EXAMPLE 2

The inventors evaluated various ingredients and processes to overcome the platelet interference. Among the experiments conducted, the inventors evaluated $Ca^{2+}$ chelators, such as EDTA. Such use of EDTA is not preferred at many laboratories, and in any event, the combination of a sample comprising platelets with EDTA alone did not reduce the role of platelet interference. Also, because heparin tubes represent a more generally suitable solution in the laboratory and clinical setting, the inventors evaluated the effects of using lithium heparin sample tubes on platelet interference. The use of lithium heparin alone in combination with samples comprising platelets did not reduce platelet interference.

EXAMPLE 3

Diazolidinyl urea (1-(1,3-Bis(hydroxymethyl-2,5-dioxoimidazolidin-4-iyl)-1,3-bis(hydroxymethyl) urea) ("DZU") has been used as an anti-coagulant in hematology for preserving white blood cells and as an anti-microbial preservative in cosmetic products, but previously has not been used to reduce platelet interference in analyte assays in the manner of the present invention. To test the effect of the addition of DZU on the incidence of platelet interference on a common immunoassay, DZU was added to plasma samples, which were then tested for hCG. The final concentration of DZU in the plasma samples was 50 mg/mL. To evaluate whether platelet interference could be reduced even when using a different centrifugation time regime, the experiment used a reduced centrifugation time (10 minutes) as compared with the recommended centrifugation time (20 minutes) at 2,200 g for preparing samples comprising platelets for immunoassay.

Two samples of blood were drawn from 51 normal, non-pregnant female donors into lithium heparin tubes. Both tubes were centrifuged immediately for 10 min at 2200 g. After centrifugation, one of the tubes was left undisturbed and the other was inverted gently ten times to disturb the settled cells in the plasma. The purpose of the inversions was to simulate the "worst case scenario" of sample disturbance, for example, as a result of mishandling. The samples (four replicates for each sample) were assayed on ADVIA® IMS using both hCG (without DZU) and hCG (with DZU) methods. The international standard for hCG recovery, 10 mIU/mL, was used as the cut-off value for the hCG assays.

It was found that DZU was effective in reducing platelet interference. Experiments demonstrated that when DZU was added to "platelet rich" plasma samples, false positive results for hCG were eliminated (see Tables 1 and 2, below). The results provided in Table 1 demonstrates that the addition of DZU is capable of diminishing false positive results as compared to the control sample as well as of counteracting the false positive results (81.4%) due to inversion of the sample that did not contain DZU.

TABLE 1

| | hCG assay without DZU | | hCG assay with diluent containing DZU (50 mg/mL) | | | |
|---|---|---|---|---|---|---|
| | | | Lot A | | Lot B | |
| | Inverted | Control | Inverted | Control | Inverted | Control |
| # donor | | | 51 | | | |
| # observation | 204 | 204 | 204 | 204 | 204 | 204 |
| # >10 mIU/mL | 166 | 21 | 0 | 0 | 0 | 0 |
| % false positive | 81.40% | 10.30% | 0% | 0% | 0% | 0% |

Table 2, below, provides hCG recovery values from specimens collected in blood sample collection tubes with and without added DZU (at 50 mg/mL final concentration).

TABLE 2

| | hCG Concentration (mIU/ml) | | | | | |
|---|---|---|---|---|---|---|
| | Donor 1 | | Donor 2 | | Donor 3 | |
| | w/o DZU | With DZU | w/o DZU | With DZU | w/o DZU | With DZU |
| Before Inversion | 0.02 | 0.00 | 0.07 | 0.10 | 0.24 | 0.15 |
| | 0.07 | 0.01 | 0.10 | 0.01 | 0.29 | 0.18 |
| | 0.07 | 0.03 | 0.01 | 0.03 | 0.19 | 0.08 |
| After Inversion | 92.95 | 0.05 | 54.20 | 0.01 | 4.17 | 0.17 |
| | 66.70 | 0.09 | 9.74 | 0.11 | 2.82 | 0.10 |
| | 32.22 | 0.00 | 19.74 | 0.11 | 8.3 | 0.10 |

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

What is claimed is:

1. A method of reducing platelet interference in an assay, comprising: contacting a sample comprising platelets with a composition comprising diazolidinyl urea to inhibit platelet activation in the sample, thereby forming a combination; and, measuring at least one analyte present in the sample in said combination.

2. The method according to claim 1 wherein said measuring at least one analyte is performed using one or more immunoassays.

3. The method according to claim 2 wherein at least one of said one or more immunoassays is an assay that is performed within a short period of time following sample acquisition.

4. The method according to claim 1 wherein said at least one analyte is human choriongonadotropin.

5. The method according to claim 1 wherein said at least one analyte is a cardiac marker.

6. The method according to claim 1 wherein said combination comprises from about 1.5 weight percent to about 7 weight percent diazolidinyl urea, wherein weight percents are based upon the total weight of said combination.

7. The method according to claim 1 wherein said combination comprises from about 3 weight percent to about 7 weight percent diazolidinyl urea, wherein weight percents are based upon the total weight of said combination.

8. The method according to claim 1 wherein said combination comprises from about 3 weight percent to about 6 weight percent diazolidinyl urea, wherein weight percents are based upon the total weight of said combination.

9. The method according to claim 1 wherein said combination comprises from about 4.5 weight percent to about 5.5 weight percent diazolidinyl urea, wherein weight percents are based upon the total weight of said combination.

* * * * *